(12) United States Patent
Perricaudet et al.

(10) Patent No.: US 7,033,826 B2
(45) Date of Patent: *Apr. 25, 2006

(54) RECOMBINANT ADENOVIRUSES, USE THEREOF FOR PREPARING AAVS, COMPLEMENTARY CELL LINE, AND PHARMACEUTICAL COMPOSITIONS CONTAINING SAID ADENOVIRUSES

(75) Inventors: Michel Perricaudet, Ecrosnes (FR); Martine Latta, Charenton le Pont (FR); Edouard Prost, Sucy en Brie (FR); Patrice Yeh, Paris (FR); Cécile Orsini, Paris (FR); Emmanuelle Vigne, Ivry Sur Seine (FR)

(73) Assignee: Aventis Pharma S.A., Antony (FR)

( * ) Notice: Subject to any disclaimer, the term of this patent is extended or adjusted under 35 U.S.C. 154(b) by 167 days.

This patent is subject to a terminal disclaimer.

(21) Appl. No.: 10/121,616

(22) Filed: Apr. 15, 2002

(65) Prior Publication Data

US 2003/0039634 A1    Feb. 27, 2003

Related U.S. Application Data

(62) Division of application No. 08/981,354, filed as application No. PCT/FR96/00968 on Jun. 20, 1996, now Pat. No. 6,420,170.

(30) Foreign Application Priority Data

Jun. 23, 1995    (FR) .................................. 95 07570

(51) Int. Cl.
*C12N 15/861*    (2006.01)
*C12N 15/864*    (2006.01)
*C12N 15/63*    (2006.01)

(52) U.S. Cl. ................. 435/320.1; 536/23.1; 536/23.7; 536/23.72; 536/24.1

(58) Field of Classification Search ............. 435/320.1, 435/69.1, 455, 456, 235.1; 536/23.1, 23.72, 536/24.1, 23.2
See application file for complete search history.

(56) References Cited

U.S. PATENT DOCUMENTS

| 5,639,661 | A | 6/1997 | Welsh et al. |
| 5,698,443 | A | 12/1997 | Henderson et al. |
| 5,756,283 | A | 5/1998 | Wilson et al. |
| 5,814,618 | A | 9/1998 | Bujard et al. |
| 6,110,744 | A | 8/2000 | Fang et al. |

FOREIGN PATENT DOCUMENTS

| FR | 2 707 664 | 1/1995 |
| WO | WO 94/12649 | 6/1994 |
| WO | WO 94/28152 | 12/1994 |
| WO | WO 95/02697 | 1/1995 |
| WO | WO 95/06743 | 3/1995 |
| WO | WO 95/20671 | 8/1995 |
| WO | WO 95/23867 | 9/1995 |
| WO | WO 96/01313 | 1/1996 |

OTHER PUBLICATIONS

Kremer et al., Adenovirus and adeno-associated virus mediated gene transfer, British Medical Bulletin 51(1):31-44 (1995).
Ko et al., A Highly Inducible System of Gene Expression by Positive Feedback Production of Glucocorticoid Receptors, DNA 8(2): 127-134 (1989).
Gossen et al., Exploiting Prokaryotic Elements For The Control Of Gene Activity In Higher Eukaryotics, JournalCellular biochemistry Suppl. 21 A:335 (1995).
Deuschle et al., Tetracycline-Reversible Silencing of Eukaryotic Promoters, Molecular & Cellular Biology 15(4): 1907-1914 (1995).
Kim et al., Tetracycline Repressor-Regulated Gene Repression in Recombinant Human Cytomegalovirus, Journal of Virology 69(4): 2565-2573 91995).
Rolling et al., AAV as a Viral Vector for Human Gene Therapy, Molecular Biotechnology 3(1):9-15 (1995).
Hersh et al., Modulation of gene expression after replication-deficient, recombinant adenovirus-mediated gene transfer by the product of a second adenovirus vector, Gene Therapy 2(2): 124-131 (1995).
Gossen et al., Transcriptional Activation by Tetracyclines in Mammalian Cells, Science 268: 1766-1769 (1995).
W. French Anderson, Nature, vol. 392, pp. 25-30, Apr. 30, 1998.
Ross et al., Human Gene Therapy, vol. 7, pp. 1781-1790, Sep. 10, 1996.
Verma et al., Nature, vol. 389, pp. 239-242, Sep. 18, 1997.
Zhang et al., PNAS, vol. 93, pp. 4513-4518, Apr. 1996.
Orken et al., "Report and Recommendations of the Panel to Assess the NIH Investment in Research on Gene Therapy," Dec. 7, 1995.
Siders et al., Cancer Research, vol. 56, pp. 5638-5646, Dec. 15, 1996.
Tanaka et al., Cancer Research, vol. 56, pp. 1341-1345, Mar. 15, 1996.
Boucher, TIG, vol. 12, No. 3, pp. 81-84, Mar. 1996.

*Primary Examiner*—David Guzo
(74) *Attorney, Agent, or Firm*—Wiley Rein & Fielding LLP

(57) ABSTRACT

A recombinant adenovirus in which the expression of a nucleic acid sequence coding for at least one homologous or heterologous gene of viral origin is placed under the control of an inducible promoter, is disclosed. The use of such recombinant adenoviruses for preparing AAVs, and a complementary cell line and preparation method therefor, are also disclosed. Furthermore, pharmaceutical compositions containing such an adenovirus are disclosed.

10 Claims, 3 Drawing Sheets

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
      (A) LENGTH: 61 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 1:

GATCCGGTCG CTCGGTGTTC GAGGCCACGC GTCACCTTAA TATGCGAAGT GGACCTCGGA      60

C      61

(2) INFORMATION FOR SEQ ID NO: 2:

(i) SEQUENCE CHARACTERISTICS:
      (A) LENGTH: 64 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 2:

AGATCTGCGG TCCGAGGTCC ACTTCGCATA TTAAGGTGAC CGTGGCCTCG ACACCGAGCG      60

ACCG      64

(2) INFORMATION FOR SEQ ID NO: 3:

(i) SEQUENCE CHARACTERISTICS:
      (A) LENGTH: 67 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 3:

CGATACTTTT CTCTATCACT GATAGGGAGT GGTCTCGAGA CTTTTCTCTA CACTGATAGG    60

GAGTGGT    67

(2) INFORMATION FOR SEQ ID NO: 4:

(i) SEQUENCE CHARACTERISTICS:
            (A) LENGTH: 75 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 4:

CGCAGATCTA CCACTCCCTA TCAGTGATAG AGAAAAGTCT CGAGACCACT CCCTATCAGT    60

GATAGAGAAA AGTAT    75

(2) INFORMATION FOR SEQ ID NO: 5:

(i) SEQUENCE CHARACTERISTICS:
            (A) LENGTH: 141 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 5:

ATCGATACTT TTCTCTATCA CTGATAGGGA GTGGTCTCGA GACTTTTCTC TATCACTGAT    60

AGGGAGTGGT AGATCTGCGG TCCGAGGTCC ACTTCGCATA TTAAGGTGAC GCGTGGCCTC    120

GAACACCGAG CGACCGGATC C    141

(2) INFORMATION FOR SEQ ID NO: 6:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 6:

GAATTCTTTT GAAGCGGGAG GTTTGAACGC G    31

(2) INFORMATION FOR SEQ ID NO: 7:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 7:

CTCCATGTAC CTGGCTGA    18

(2) INFORMATION FOR SEQ ID NO: 8:

(i) SEQUENCE CHARACTERISTICS:
            (A) LENGTH: 206 amino acids

-continued

```
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 8:

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Leu Leu Gly Val Glu Gln Pro Thr Leu Tyr Trp His Val Lys Asn Lys
            35                  40                  45

Arg Ala Leu Leu Asp Ala Leu Ala Ile Glu Met Leu Asp Arg His Thr
        50                  55                  60

His Phe Cys Pro Leu Lys Gly Glu Ser Trp Gln Asp Phe Leu Arg Asn
65                  70                  75                  80

Asn Ala Lys Ser Phe Arg Cys Ala Leu Leu Ser His Arg Asn Gly Ala
                85                  90                  95

Lys Val His Ser Glu Thr Arg Pro Thr Glu Lys Gln Tyr Glu Thr Leu
            100                 105                 110

Glu Asn Gln Leu Ala Phe Leu Cys Gln Gln Gly Phe Ser Leu Glu Asn
            115                 120                 125

Ala Leu Tyr Ala Leu Ser Ala Val Gly His Phe Thr Leu Gly Cys Val
        130                 135                 140

Leu Glu Asp Gln Glu His Gln Val Ala Lys Glu Glu Arg Glu Thr Pro
145                 150                 155                 160

Thr Thr Asp Ser Met Pro Pro Leu Leu Arg Gln Ala Ile Glu Leu Phe
                165                 170                 175

Asp His Gln Gly Ala Glu Pro Ala Phe Leu Phe Gly Leu Glu Leu Ile
            180                 185                 190

Ile Cys Gly Leu Glu Lys Gln Leu Lys Cys Glu Ser Gly Ser
            195                 200                 205
```

RECOMBINANT ADENOVIRUSES, USE THEREOF FOR PREPARING AAVS, COMPLEMENTARY CELL LINE, AND PHARMACEUTICAL COMPOSITIONS CONTAINING SAID ADENOVIRUSES

REFERENCE TO RELATED APPLICATIONS

This application is a divisional application of and claims the priority benefit of U.S. application Ser. No. 08/981,354, now U.S. Pat. No. 6,420,170, filed Dec. 19, 1997, which claims the benefit of PCT application PCT/FR96/00968, filed Jun. 20, 1996, which claims the benefit of prior French application FR 95 07570 filed Jun. 23, 1995.

The present invention relates to new viral vectors, to their preparation and to their uses. It also relates to pharmaceutical compositions containing the said viral vectors.

Gene therapy consists in correcting a deficiency or an abnormality (mutation, aberrant expressions, and the like) by introducing genetic information into the cell or organ affected. This genetic information may be introduced either in vitro into a cell extracted from the organ, the modified cell then being reintroduced into the body, or directly in vivo into the appropriate tissue. In this second case, different techniques exist, including various techniques of transfection involving complexes of DNA and DEAE-dextran (Pagano et al., J. Virol. 1 (1967) 891), of DNA and nuclear proteins (Kaneda et al., Science 243 (1989) 375) and of DNA and lipids (Felgner et al., PNAS 84 (1987) 7413), the use of liposomes (Fraley et al., J. Biol. Chem. 255 (1980) 10431), and the like.

More recently, the use of viruses as vectors for gene transfer has been seen to be a promising alternative to these physical transfection techniques. In this connection, different viruses have been tested for their capacity to infect certain cell populations. This applies especially to retroviruses (RSV, HMS, MMS, and the like), the HSV virus, adeno-associated viruses and adenoviruses.

As regards adenoviruses more especially, the latter are linear double-stranded DNA viruses approximately 36 kb in size. Their genome comprises, in particular, an inverted sequence (ITR) at each end, an encapsidation sequence, early genes and late genes (see FIG. 1). The main early genes are contained in the E1, E2, E3 and E4 regions. Among them, the genes contained in the E1 region (E1a and E1b, in particular) are necessary for viral replication. The E4 and L5 regions, for example, are involved in viral propagation, and the main late genes are contained in the L1 to L5 regions. The Ad5 adenovirus genome has been sequenced completely and is available on a database (see, in particular, Genebank M73260). Similarly, portions, or in some cases the whole, of the genome of adenoviruses of different serotypes (Ad2, Ad7, Ad12, and the like) have also been sequenced. These viral vectors advantageously display a fairly broad host range, are capable of infecting quiescent cells, do not integrate in the genome of the infected cell and have not been hitherto associated with significant pathologies in man. In view of their properties, they have already been used for gene transfer in vivo. To this end, different vectors derived from adenoviruses have been prepared, incorporating different genes (β-gal, OTC, $\alpha_1$-AT, cytokines, and the like).

Naturally, all of these viral vectors contain numerous viral genes whose expression is, on the other hand, not desirable in gene therapy. It is essential to control in vivo the non-expression of wild-type viral genes and/or of proteins which are derived therefrom and which are liable to induce an immune and/or inflammatory response which is undesirable or even thoroughly deleterious with respect to the body being treated.

For these purposes, the viral vector constructions currently proposed are modified so as to render the said vectors incapable of replicating autonomously in the target cell. They are said to be defective. Generally, the genome of defective viruses hence lacks at least the sequences necessary for replication of the said virus in the infected cell. These regions may be either removed (wholly or partially), or rendered non-functional, or replaced by other sequences, and in particular by a sequence coding for a molecule of therapeutic interest. Preferably, the defective virus nevertheless retains the sequences of its genome which are necessary for encapsidation of the viral particles.

In the particular case of recombinant adenoviruses, the constructions described in the prior art are generally adenoviruses from which the E1 (E1a and/or E1b) and possibly E3 regions have been deleted, in which regions the heterologous DNA sequences are inserted (Levrero et al., Gene 101 (1991) 195; Gosh-Choudhury et al., Gene 50 (1986) 161). Other constructions contain a deletion in the E1 region and of a non-essential portion of the E4 region (WO 94/12649). These defective recombinant adenoviruses may be prepared in different ways, employing or otherwise a competent cell line capable of complementing all the defective functions essential for replication of the recombinant adenovirus. At the present time, the vectors derived from adenoviruses are generally produced in a complementation line (line 293) in which a portion of the adenovirus genome has been integrated. More specifically, line 293 contains the left-hand end (approximately 11–12%) of the adenovirus serotype 5 (Ad5) genome, comprising the left-hand ITR, the encapsidation region and the E1 region, including E1a, E1b and a portion of the region coding for the pIX protein. This line is capable of trans-complementing recombinant adenoviruses which are defective for the E1 region, that is to say lacking all or part of the E1 region, necessary for replication.

However, during the production of these defective viral vectors, it is not possible to rule out completely the possibility of recombinations generating replicative viral particles, or in vivo trans-complementations by E1 type cellular functions. It is obvious that this type of event is completely incompatible with their subsequent use in gene therapy. The presence in vivo of replicative viral particles may have highly deleterious consequences, such as, for example, the induction of a viral propagation and production of an uncontrolled dissemination with risks of inflammatory reaction, recombination, and the like.

Concomitantly, it is essential to prevent in vivo the expression of corresponding viral proteins. Although the latter do not necessarily display a toxic character with respect to the cell, they are also highly undesirable since they are also liable to induce immune system responses of the inflammation type and/or fevers which are detrimental to the body being treated (D. Y. Schwarz, (1995), P.N.A.S. 92, 1401–1405; J. F. Engelhardt, (1994), Human Gene Therapy, 5, 1217–1229 and (1994) P.N.A.S. 91, 6196–6200; Y. Yang, (1994), Immunity, 1, 433–442, (1995) J; Virol., 69, 2004–2015 and Nature Genetics, (1994) 7, 362–369).

The objective of the present invention is specifically to provide an approach enabling these drawbacks to be remedied, and the invention proves most especially useful for preparing batches of adenovirus type viruses displaying enhanced safety since, in particular, they lack replicative viral particles.

Unexpectedly, the Applicant demonstrated that it was possible, using a novel promoter system, to control effectively the expression of viral gene, which expression is effective in vitro during viral production but, on the other hand, subsequently ineffective in vivo when the said recombinant viruses are used therapeutically.

More specifically, the present invention relates to a recombinant adenovirus in which the expression of at least one homologous or heterologous gene of viral origin is controlled by an inducible promoter.

For the purposes of the present invention, inducible promoter is understood to mean any promoter whose activity is initiated by the presence of an external chemical and/or biological agent, which agent, in the context of the present invention, displays, in addition, low or even zero toxicity. "External" is understood to mean that the chemical and/or biological agent does not naturally exist in the cells treated with the claimed adenovirus.

As inducible promoters capable of being employed according to the present invention, traditional promoters such as those responding to heavy metals (CRC Boca Raton, Fla. (1991), 167–220; Brinster et al. Nature (1982), 296, 39–42), to thermal shocks, to hormones (Lee et al. P.N.A.S. USA (1988), 85, 1204–1208; (1981), 294, 228–232; Klock et al. Nature (1987), 329, 734–736; Israël and Kaufman, Nucleic Acids Res. (1989), 17, 2589–2604) or to chemical agents of the glucose, lactose, galactose or antibiotic type may be mentioned in particular.

Very recently, a tetracycline-inducible promoter which is especially advantageous in the context of the present invention has been described.

This promoter, termed tetracycline-inducible promoter, comprises a minimal promoter linked operationally to one or more tetracycline operator(s). The binding of a so-called "transcription activator" protein to the tetracycline operator sequences, which binding is established only in the presence of tetracycline or one of its analogues, is the event which permits the activation of the minimal promoter and hence the transcription of the associated viral gene or genes.

As regards, more especially, the so-called transcription activator protein, this is hence characterized by its ability to bind, in the presence of tetracycline, to the operator sequences of the tetracycline-inducible promoter, and its capacity to activate the minimal promoter. More preferably, the protein in question consists of two polypeptides, a first polypeptide which binds to the tet operator sequences in the presence of tetracycline or an analogue of the latter, and a second polypeptide whose function is more specifically to activate the said transcription. The first polypeptide of the so-called transcription activator protein is a tetracycline repressor mutated so as to manifest a behaviour opposite to that of a wild-type repressor, that is to say it binds to the tet operator sequences only in the presence and not in the absence of tetracycline. As regards the second polypeptide, this is preferably the activation domain of herpes simplex virus protein 16.

In the case where the inducible promoter used is, for example, inducible with glucose or galactose, it is possible to envisage employing a transcription activator constructed on this model, that is to say, for example, Glu-VP16 or Gal4-VP16.

According to a preferred embodiment of the invention, the inducible promoter employed is a promoter which is inducible with tetracycline or one of its analogues, as described above.

For the purposes of the present invention, a tetracycline-inducible promoter comprises a minimal promoter linked operationally to a so-called regulatory sequence comprising at least one operator for tetracycline, "tet operator", or for one of its analogues.

Tetracycline analogue is understood to cover any compound displaying structural homologies with tetracycline and which is capable of binding to its receptor bound to the trans-activation domain of the so-called transcription activator protein presented above, with a Ka of at least approximately $10^6$ $M^{-1}$. As analogues capable of being used according to the present invention, doxycycline, chlorotetracycline and anhydrotetracycline may be mentioned in particular.

Minimal promoter is understood to denote any promoter sequence which, on its own, is not capable of effectively procuring the transcription of the DNA sequence which is associated with it. The activity of such a promoter proves to be completely dependent on the binding of the transcription activator protein to the so-called regulatory sequence in the presence of tetracycline. In fact, this minimal promoter has above all the function of orienting the transcription. From this standpoint, it is preferably located upstream of the viral sequence so as to form a continuous nucleotide sequence with the latter.

This minimal promoter may be derived from the human cytomegalovirus immediate-early promoter, and more preferably lies between nucleotides +75 and −53 or +75 and −31. However, it is also possible to employ, according to the invention, a minimal promoter derived from a conventional promoter such as, for example, the one that activates the transcription of the gene coding for thymidine kinase.

A conventional promoter may also be rendered minimal by means of one or more genetic mutations which render it incapable of effectively procuring on its own the transcription of the gene which is associated with it. A minimal promoter derived directly from the promoter naturally responsible for the expression of the viral gene in question may also be employed in the context of the present invention. It is also possible to envisage the use of a so-called "TATA-less" promoter as described by E. MARTINEZ et al. (EMBO Journal, (1994), 13, No. 13, 3115–3126), so as to obtain the lowest possible background baseline in the uninduced situation.

Generally speaking, this minimal promoter is placed upstream of the nucleotide sequence whose expression it controls, as a replacement or otherwise for its natural promoter. The promoter belonging to the nucleic acid sequence can, in effect, remain present, but in a form which is inactivated or rendered non-functional by different techniques known to a person skilled in the art, and in particular by elimination, deletion and/or addition of one or more bases.

According to a particular embodiment of the invention, the minimal promoter is derived from the thymidine kinase minimal promoter of herpes simplex virus (McKnight et al. (1984) Cell 37:253–262). It is then designated Tk.

More preferably, it is represented wholly or partially by one of the sequences shown as SEQ ID No. 1 or No. 2 or one of their derivatives.

For the purposes of the present invention, the term derivative denotes any sequence obtained by modification of a genetic and/or chemical nature of given sequences and which retains the desired activity. Modification of a genetic and/or chemical nature should be understood to mean any mutation, substitution, deletion, addition and/or modification of one or more nucleic acid.

As regards the so-called regulatory sequence, this comprises at least one operator for tetracycline or one of its analogues. The operator or operators are recognized by the transcription activator in the presence of tetracycline and hence, as a result, permit the activation of the minimal promoter.

The tet operator sequences which can be employed may be chosen, in particular, from those described by Hillen and Wissemann (Protein-Nucleic Acid Interaction, Saeger and Heinemann, eds., Macmillan, London, (1989) 10, 143–162), Waters et al. (Nucleic Acids Res. (1983), 11, 525–539), Stüber et al. (P.N.A.S. USA, (1981), 78, 167–171), Unger et al. (Nucleic Acids Res. (1984), 12, 7693–7703) and Tovar et al. (Mol. Gen. Genet. (1988), 215, 76–80).

The regulatory sequence may comprise a single tet operator sequence or, on the contrary, several tet operator sequences, which can number as many as 10 depending on whether or not it is desired to increase the regulation of transcription. According to a particular embodiment of the invention, the regulatory sequence employs 2 tet operator sequences. It will then be termed Op2.

More preferably, the regulatory sequence is represented wholly or partially by one of the sequences shown as SEQ ID No. 3 or No. 4 or one of their derivatives.

Traditionally, this regulatory sequence is linked operationally upstream, that is to say at the 5' end of the minimal promoter, so as to permit the transcription of the gene of viral origin in the presence of the complex formed by the transcription activator and its tetracycline ligand. The structure thus comprises, successively, in the 5' to 3' orientation, the regulatory sequence, bound directly or otherwise to the minimal promoter, the minimal promoter and the gene of viral origin. However, it is also possible to envisage placing this regulatory sequence, within the minimal promoter, downstream of the viral nucleotide sequence to be transcribed, that is to say at its 3' end. The order of succession is then, in the 5' to 3' direction, minimal promoter, viral gene and regulatory sequence.

According to a preferred embodiment of the invention, the tetracycline-inducible promoter links a regulatory sequence represented by Op2 to the thymidine kinase minimal promoter termed Tk. It is in this particular case identified below under the name Op2/Tk. More preferably, the inducible promoter employed according to the invention is represented wholly or partially by SEQ ID No. 5 or one of its derivatives.

This tetracycline-inducible promoter Op2/Tk, and more especially the one represented wholly or partially by SEQ ID No. 5 or one of its derivatives, also constitute one of the subjects of the present invention.

Consequently, the expression of the viral gene or genes linked operationally, in the claimed adenovirus, to an inducible promoter is completely dependent on the binding of the complex formed by the transcription activator and tetracycline to the regulatory sequence of the said promoter.

This binding is effective only in the presence of tetracycline. In the absence of tetracycline or of any analogue of the latter, no binding is established between the regulatory sequence and the transcription activator. No transcription of the viral sequence bound to the minimal promoter ensues. What is more, advantageously, the agent inducing transcription does not have to be present continuously.

One of the subjects of the present invention relates more especially to an adenovirus comprising at least one homologous, that is to say adenoviral, gene whose expression is controlled by an inducible promoter, and more preferably by a tetracycline-inducible promoter.

Thus, in a particular embodiment, the subject of the present invention is a recombinant adenovirus in which at least one genomic region essential for viral replication and/or propagation is placed wholly or partially under the control of a tetracycline-inducible promoter. The region essential for viral replication and/or propagation according to the present invention is advantageously chosen from all or part of the E4, E2 region, the IVa2 region and/or the L5 region, and the like.

According to an especially advantageous embodiment, the recombinant adenoviruses of the present invention comprise all or a functional portion of the E2 or E4 regions as sequences necessary for replication and/or propagation. More especially, as regards the E4 region, the important genes are the ORF3, ORF6 and ORF6/7 genes.

The E2 region is involved in the regulation of the viral DNA. This E2 region consists of two transcription subunits E2A and E2B.

The E4 region is involved in regulation of the expression of the late genes, in the stability of the late nuclear RNAs, in abolishing the expression of the host cell's proteins and in the efficacy of the replication of the viral DNA. Mutants lacking E4 are incapable of propagating. E4 thus constitutes a region essential for viral propagation. This E4 region consists of 7 open reading frames, designated ORF1, ORF2, ORF3, ORF4, ORF3/4, ORF6 and ORF6/7 (FIG. 2). Among these, ORF3 and ORF6 are the two genes essential for viral propagation. Each of these genes is capable of inducing viral propagation, ORF6, however, playing a larger part therein than ORF3 (Huang and Hearing (1988), J. Virol. 63, 2605).

In a particular embodiment, in the vectors of the invention, the whole of the region in question is placed under the control of a tetracycline-inducible promoter. In the particular case of the E2 region, the region in question can be a fragment corresponding to the 72K cDNA, to the 140K polymerase cDNA or to the 87K pre-terminal protein cDNA. As regards the E4 region, the region in question can be, in particular, the Taq1-Bgl2 fragment corresponding to nucleotides 35576-32490.

In another particular embodiment, only the expression of a functional portion of these regions, that is to say sufficient to permit viral propagation, is controlled. In the particular case of E4, this portion comprises at least one functional ORF3 or ORF6 gene. Preferably, the functional portion of E4 consists essentially of ORF6. As an example, the Bgl2 fragment, lying between positions 34115 and 32490 and containing the sequences of the ORF6 and ORF7 of Ad5, may be positioned downstream of an inducible promoter as defined according to the invention.

In another particular embodiment of the present invention, the essential region consists of the region coding for the IVa2 protein, and for example its cDNA. In another embodiment, the region coding for the IVa2 protein is included in a BglII-NruI fragment corresponding to nucleotides 3328 to 6316 on the wild-type Ad5 adenovirus sequence, a DraI-NlaIII fragment corresponding to nucleotides 4029 to 5719 or a DraI to XhoI fragment corresponding to nucleotides 4029 to 5788.

According to a preferred embodiment of the invention, the promoters of the regions essential for viral propagation are replaced within the viral genome by an inducible promoter, and more preferably by a tetracycline-inducible promoter.

In a first particular embodiment, the recombinant adenoviruses of the invention carry a deletion of all or part of the E1 gene and possess the E4 region, wholly or partially, under the control of a tetracycline-inducible promoter, preferably of the Op2/Tk type.

In another particular embodiment, the recombinant adenoviruses of the invention carry a deletion of all or part of the E1 gene and possess the E2 region wholly or partially under the control of a tetracycline-inducible promoter, preferably of the Op2/Tk type.

Still according to a preferred embodiment, the recombinant adenoviruses of the invention carry a deletion of all or part of the E1 and E2 genes and possess the E4 region wholly or partially under the control of a tetracycline-inducible promoter, preferably of the Op2/Tk type.

In an especially advantageous variant, the recombinant adenoviruses of the invention carry a deletion of all or part of the E1 and E4 genes and possess the E2 region wholly or partially under the control of a tetracycline-inducible promoter, preferably of the Op2/Tk type.

Advantageously, the recombinant adenoviruses of the invention contain, in addition, a heterologous nucleic acid sequence containing one or more therapeutic genes whose transfer to a cell, organ or body and/or expression therein is sought.

Therapeutic genes which may be transferred in this way are any gene whose transcription and, where appropriate, translation in the target cell generate products having a therapeutic effect.

Such genes can be, in particular, ones coding for proteinaceous products having a therapeutic effect. The proteinaceous product thus encoded can be a protein, a peptide, and the like. This proteinaceous product can be homologous with respect to the target cell (that is to say a product which is normally expressed in the target cell when the latter does not display any pathology). In this case, the expression of a protein makes it possible, for example, to compensate for an insufficient expression in the cell or for the expression of a protein that is inactive or poorly active as a result of a modification, or alternatively to overexpress the said protein. The therapeutic gene can also code for a mutant of a cellular protein, having enhanced stability, modified activity, and the like. The proteinaceous product can also be heterologous with respect to the target cell. In this case, an expressed protein can, for example, supplement or supply an activity which is deficient in the cell, enabling it to combat a pathology.

Among products which are therapeutic for the purposes of the present invention, there may be mentioned, more especially, enzymes, blood derivatives, hormones, lymphokines, namely interleukins, interferons, TNF, and the like (FR 92/03120), growth factors, neurotransmitters or their precursors or synthetic enzymes, trophic factors, namely BDNF, CNTF, NGF, IGF, GMF, aFGF, bFGF, NT3, NT5, and the like; apolipoproteins, namely ApoAI, ApoAIV, ApoE, and the like (FR 93/05125), dystrophin or a minidystrophin (FR 91/11947), tumour-suppressing genes, namely p53, Rb, Rap1A, DCC, k-rev, and the like (FR 93/04745), genes coding for factors involved in coagulation, namely factors VII, VIII, IX, and the like, suicide genes, namely thymidine kinase; cytosine deaminase, and the like; or alternatively all or part of a natural or artificial immunoglobulin (Fab, ScFv, and the like), and the like.

The therapeutic gene can also be an antisense gene or sequence whose expression in the target cell enables the expression of cellular genes or the transcription of cellular mRNA to be controlled, for instance ribozymes. Such sequences can, for example, be transcribed in the target cell into RNAs complementary to cellular mRNAs, and can thus block their translation into protein, according to the technique described in Patent EP 140,308.

The therapeutic gene can also be a gene coding for an antigenic peptide capable of generating an immune response in man. In this particular embodiment, the invention hence makes it possible to produce vaccines enabling humans to be immunized, in particular against microorganisms or viruses. Such antigenic peptides can be, in particular, specific to the Epstein-Barr virus, the HIV virus, the hepatitis B virus (EP 185,573) or the pseudorabies virus, or alternatively tumour-specific (EP 259,212).

Generally, the heterologous nucleic acid sequence also comprises a transcription promoter region which is functional in the infected cell, as well a region located at the 3' end of the gene of interest and which specifies a transcription termination signal and a polyadenylation site. These elements collectively constitute the expression cassette. As regards the promoter region, this can be a promoter region naturally responsible for the expression of the gene in question when the region is capable of functioning in the infected cell. Regions of different origin (responsible for the expression of other proteins, or even synthetic) are a further possibility. In particular, such regions can be promoter sequences of eukaryotic or viral genes. For example, they can be promoter sequences originating from the genome of the cell which it is desired to infect. Similarly, they can be promoter sequences originating from the genome of a virus, including the adenovirus used. In this connection, the promoters of E1A, MLP, CMV, RSV, and the like, genes may be mentioned as examples. In addition, these promoter regions may be modified by the addition of activator or regulatory sequences or sequences permitting a tissue-specific or -preponderant expression. Moreover, when the heterologous nucleic acid does not contain promoter sequences, it may be inserted into the genome of the defective virus downstream of such a sequence.

Moreover, the heterologous nucleic acid sequence can also contain, especially upstream of the therapeutic gene, a signal sequence directing the therapeutic product synthesized into the pathways of secretion of the target cell. This signal sequence can be the natural signal sequence of the therapeutic product, but it can also be any other functional signal sequence, or an artificial signal sequence.

This nucleic acid sequence is preferably present in the E1, E3 or E4 regions, in addition or as a replacement for deleted sequences.

A second main subject of the present invention is an adenovirus containing at least one heterologous gene of viral origin whose expression is controlled by an inducible promoter, and more preferably a tetracycline-inducible promoter.

According to a preferred embodiment of the invention, the heterologous gene of viral origin is or is derived from a gene of the genome of an AAV or one of its functional homologues.

AAVs are relatively small-sized DNA viruses which integrate in the genome of the cells they infect, stably and site-specifically. They are also capable of infecting a broad range of cells without inducing an effect on cell growth, morphology or differentiation. Moreover, they appear not to be involved in pathologies in man. The AAV genome has been cloned, sequenced and characterized. It comprises 4,680 bases, and contains an inverted repeat region (ITR) of approximately 145 bases at each end, serving as origin of replication for the virus. The remainder of the genome is divided into two essential regions carrying the encapsidation functions: the left-hand portion of the genome, which contains the rep gene involved in viral replication and the expression of the viral genes; the right-hand portion of the genome, which contains the cap gene coding for the capsid proteins of the virus. Three promoters have been localized therein and named according to their approximate position in map units p5, p19 and p40. Four proteins are at least synthesized from the rep region and have been named on the basis of their apparent molecular mass Rep78, Rep68, Rep52 and Rep40. The 2 mRNAs transcribed from the p5 promoter are used for the synthesis of Rep78 and Rep68. Rep52 and Rep40, for their part, are synthesized from messengers originating from the p19 promoter. As regards the cap gene more especially, this codes for the envelope proteins of the virus (VP1, VP2 and VP3). VP3 is the preponderant capsid protein, and its amino acid sequence is contained in those of two larger but less abundant proteins VP1 and VP2 (make a diagram). The rep and cap genes have been characterized and their respective sequences described in the literature (Srivastava et al., J. Virol. 45 (1983) 555).

The use of vectors derived from AAVs for gene transfer in vitro and in vivo has been described in the literature (see, in particular, WO 91/18088; WO 93/09239; U.S. Pat. Nos. 4,797,368, 5,139,941, EP 488,528). Generally, the constructions used in gene therapy contain a deletion of the rep and/or cap genes which are replaced by a gene of interest.

In order to replicate, AAVs require the presence of a helper virus capable of trans-complementing the functions necessary for their replication. This can be, in particular, an adenovirus, a herpesvirus or a vaccinia virus. (In the absence of such a helper virus, AAVs remain in latent form in the genome of infected cells, but cannot replicate and thus cannot produce viral particles.) Traditionally, recombinant AAVs are hence produced by cotransfection, into a cell line infected with a human helper virus (for example an adenovirus), of a plasmid containing the gene of interest flanked by two AAV inverted repeat regions (ITR) and a plasmid carrying the AAV encapsidation genes (rep and cap genes). Coinfection with the adenovirus initiates a cascade of events which end in the production of high titres of AAV and substantially decrease the production of adenovirus. This cascade starts with the synthesis of the product of the E1a gene, which induces transcription from the p5 and p19 promoters and leads to the synthesis of a small amount of Rep proteins. One or more Rep proteins synthesized from p5 then induce the synthesis of mRNA in more abundant amounts from the 3 promoters at a much greater level and in a coordinated manner. In the absence of adenovirus, the AAV genome is either lost or integrated in the host's chromosome. Genes other than E1A of the adenovirus are also necessary for an effective expression of the AAV genes.

Advantageously, the Applicant demonstrated that it was possible to place effectively at least the expression of one of the viral genes of the AAV under the control of an inducible promoter in an adenovirus, and more preferably to control the expression of the AAV encapsidation functions, especially the expression of the rep and/or cap genes, or of any functional homologous gene.

A functional homologue corresponds to any gene obtained by modification (mutation, elimination, addition, and the like) of the rep or cap genes and displaying an activity of the same nature. Such functional homologous genes can also be genes obtained by hybridization from nucleic acid libraries by means of probes corresponding to the rep or cap genes. As a mutated rep gene capable of being controlled according to the invention, its mutant in1177 described in the publication Y. Yang et al. ((1992) Journal of virology, 6058–6069), and derived from an insertion of serines between codons 286 and 287, may be mentioned more especially.

According to a preferred embodiment of the invention, the inducible promoter employed is a tetracycline-inducible promoter as defined above.

Such an adenovirus is advantageous in several ways: from the standpoint of manipulations, it considerably simplifies the method for preparing stocks of AAV. In effect, in this particular case, essentially only the said adenovirus containing the rep and cap genes under the control of the inducible promoter, a recombinant AAV and an appropriate cell line are employed. Lastly, the expected titres of AAV from such an adenovirus prove greater than those obtained according to a conventional method.

The inducible promoter can, in particular, be introduced as a replacement for one of the promoters normally leading to the expression of the gene or genes in question, and especially as a replacement for the p5, p19 or p40 promoter. Since the p5 promoter appears to be the one most involved in the initiation of the cascade of events leading to the production of the virus, its replacement by a tetracycline-inducible promoter, preferably of the Op2/Tk type, is more preferably undertaken. Advantageously, such a construction enables the expression of rep and cap to be blocked in the absence of tetracycline.

The AAV encapsidation functions under the control of an inducible promoter may be introduced into different regions of the genome of the claimed adenovirus. Advantageously, the encapsidation functions are inserted into a region which does not interfere with the capacity of the virus to trans-complement AAVs. It is also possible to insert the encapsidation functions into a functional region of the genome of the said adenovirus, this region then being supplied in trans, either by a plasmid or by the cell line used. It is possible, for example, to insert the rep gene, the cap gene or the rep and cap genes in the E1 or E3 regions as a replacement for or in addition to the deleted sequences.

In order to abolish any transcriptional leakage due to the proximity of the ITR-psi region, a so-called negative regulatory sequence may, in addition, be introduced. Such a sequence inserted, in particular, between the left-hand ITR and the psi sequence of the claimed adenovirus on the one hand, and the sequence coding for the tetracycline-inducible promoter, makes it possible to curb any spurious transcriptional activation of rep and cap induced, where appropriate, by the enhancer located in the left-hand ITR of the adenovirus and the psi sequence. As negative sequences which may be employed according to the invention, those identified in the vimentin promoter (Salvetti et al. (1993), Mol. Cell. Biol. 1676–1685), in the interferon promoter (Whitemore et al. (1990), P.N.A.S., 87, 7799–7803), in the cardiac myosin light chain 2 gene (Ruoquian-Shen et al. (1991), Mol. Cell. Biol., 1676–1685) and in the mouse albumin promoter (Herbst et al. (1990), Mol. Cell. Biol., 3896–3905) may be mentioned in particular.

According to a preferred embodiment, the invention relates to a recombinant adenovirus containing an Op2/Tk-rep-cap expression cassette.

The subject of the present invention is also the use of these adenoviruses integrating a viral sequence of AAV origin under the control of a tetracycline-inducible promoter for preparing AAVs.

In a preferred embodiment, the adenoviruses which are the subjects of the invention comprise the ITR sequence and a sequence permitting encapsidation. Preferably, these adenoviruses possess, in addition, a non-functional E1 region.

The inverted repeat sequences (ITR) constitute the origin of replication of the adenoviruses. They are localized at the 3' and 5' ends of the viral genome (see FIG. 1), from where they may be isolated readily according to the traditional techniques of molecular biology known to a person skilled in the art. The nucleotide sequence of the ITR sequences of human adenoviruses (especially of the serotypes Ad2 and Ad5) is described in the literature, as are those of canine adenoviruses (in particular CAV1 and CAV2). As regards the Ad5 adenovirus for example, the left-hand ITR sequence corresponds to the region comprising nucleotides 1 to 103 of the genome.

The encapsidation sequence (also designated psi sequence) is necessary for encapsidation of the viral DNA. This region must hence be present in order to permit the preparation of defective recombinant adenoviruses according to the invention. The encapsidation sequence is localized in the genome of the adenoviruses, between the left-hand (5') ITR and the E1 gene (see FIG. 1). It may be isolated or synthesized artificially by traditional techniques of molecular biology. The nucleotide sequence of the encapsidation sequence of human adenoviruses (especially of the serotypes Ad2 and Ad5) is described in the literature, as are those of canine adenoviruses (in particular CAV1 and CAV2). As regards the Ad5 adenovirus for example, the encapsidation sequence corresponds to the region comprising nucleotides 194 to 358 of the genome.

According to an especially advantageous embodiment, in the recombinant adenoviruses of the present invention, the E1 region is inactivated by deletion of a PvuII-BglII fragment extending from nucleotide 454 to nucleotide 3328 on the Ad5 adenovirus sequence. This sequence is available in the literature and also on a database (see, in particular, Genebank No. M73260). In another preferred embodiment, the E1 region is inactivated by deletion of a HinfII-Sau3A fragment extending from nucleotide 382 to nucleotide 3446.

The adenoviruses of the invention may be prepared from adenoviruses of diverse origins. There are, in effect, different serotypes of adenovirus, the structure and properties of which vary somewhat but which display a comparable genetic organization. Thus, the teachings described in the present application may be readily reproduced by a person skilled in the art for any type of adenovirus.

More especially, the adenoviruses of the invention may be of human, animal or mixed (human and animal) origin.

As regards adenoviruses of human origin, it is preferable to use those classified in group C. More preferably, among the different serotypes of human adenovirus, it is preferable to use adenoviruses type 2 or 5 (Ad2 or Ad5) in the context of the present invention.

As mentioned above, the adenoviruses of the invention may also be of animal origin, or may contain sequences originating from adenoviruses of animal origin. The Applicant has, in effect, shown that adenoviruses of animal origin are capable of infecting human cells with great efficacy, and that they are incapable of propagating in the human cells in which they have been tested (see Application WO 94/26914). The Applicant has also shown that adenoviruses of animal origin are in no way trans-complemented by adenoviruses of human origin, thereby eliminating any risk of recombination and propagation in vivo in the presence of a human adenovirus, which can lead to the formation of an infectious particle. The use of adenoviruses or of regions of adenoviruses of animal origin is hence especially advantageous, since the risks inherent in the use of viruses as vectors in gene therapy are even lower.

The adenoviruses of animal origin which may be used in the context of the present invention can be of canine, bovine, murine (for example: Mav1, Beard et al., Virology 75 (1990) 81), ovine, porcine, avian or alternatively simian (for example: SAV) origin. More especially, among avian adenoviruses, there may be mentioned the serotypes 1 to 10 which are available in the ATCC, such as, for example, the strains Phelps (ATCC VR-432), Fontes (ATCC VR-280), P7-A (ATCC VR-827), IBH-2A (ATCC VR-828), J2-A (ATCC VR-829), T8-A (ATCC VR-830), K-11 (ATCC VR-921) or alternatively the strains referenced ATCC VR-831 to 835. Among bovine adenoviruses, the different known serotypes may be used, and in particular those available in the ATCC (types 1 to 8) under the references ATCC VR-313, 314, 639–642, 768 and 769. There may also be mentioned the murine adenoviruses FL (ATCC VR-550) and E20308 (ATCC VR-528), ovine adenovirus type 5 (ATCC VR-1343) or type 6 (ATCC VR-1340), porcine adenovirus 5359, or simian adenoviruses such as, in particular, the adenoviruses referenced in the ATCC under the numbers VR-591–594, 941–943, 195–203, and the like.

Among the different adenoviruses of animal origin, it is preferable in the context of the invention to use adenoviruses or regions of adenoviruses of canine origin, and in particular all strains of CAV2 adenoviruses [strain Manhattan or A26/61 (ATCC VR-800) for example]. Canine adenoviruses have been subjected to many structural studies. Thus, complete restriction maps of CAV1 and CAV2 adenoviruses have been described in the prior art (Spibey et al., J. Gen. Virol. 70 (1989) 165), and the E1a and E3 genes as well as the ITR sequences have been cloned and sequenced (see, in particular, Spibey et al., Virus Res. 14 (1989) 241; Linné, Virus Res. 23 (1992) 119, WO 91/11525).

The present invention relates, in addition, to a method which is useful for the preparation of AAV.

More specifically, its subject is a method for preparing AAV, characterized in that it comprises the cotransfection, in the presence of tetracycline or one of its analogues, of a cell line comprising in its genome the cassette for the expression of a transcription activator, with an adenovirus comprising at least one gene of AAV origin under the control of a tetracycline-inducible promoter, and either a recombinant virus derived from the AAV or a plasmid carrying a transgene between the ITRs of the AAV. The adenovirus is preferably one comprising the rep and cap genes as heterologous viral genes.

The method according to the invention turns to good account the ability to induce the expression of these rep and cap genes placed under the control of a tetracycline-inducible promoter within an adenovirus, in the presence of a sufficient amount of tetracycline and a transcription activator.

As explained earlier, this method has the advantage of being simplified from the standpoint of manipulations compared to a traditional method. In the present case, all that is carried out is a coinfection of a cell line with an adenovirus such as is claimed and a recombinant virus derived from an AAV.

Besides the transformed adenovirus according to the invention, this method employs a cell line containing in its genome a cassette for the expression of the so-called transcription activator protein consisting of a first polypeptide capable of binding, in the presence of tetracycline or one of its analogues, to the regulatory sequence of the inducible promoter present in the adenovirus, combined with a second polypeptide which activates transcription.

As regards, more especially, the so-called transcription activator protein, this is hence characterized by its ability to bind, in the presence of tetracycline, to the so-called regulatory sequence and its capacity to activate the minimal promoter which is associated with it. As explained above, it is a protein consisting of two polypeptides, a first polypeptide which binds to the tet operator sequences in the presence of tetracycline or an analogue of the latter, and a second polypeptide whose function is more specifically to activate the said transcription.

According to a favoured embodiment of the invention, the first polypeptide of the so-called transcription activator protein is a tetracycline repressor mutated so as to manifest a behaviour opposite to that of a wild-type repressor, that is to say it binds to the tet operator sequences only in the presence and not in the absence of tetracycline. This type of mutation may be performed according to traditional biological techniques of the mutagenesis type. The difference in amino acids between the wild-type repressor and the mutated repressor according to the present invention can consist of a substitution, deletion and/or addition of one or more amino acids. It has the effect of endowing the repressor thus transformed with two functional properties: it can bind to the regulatory sequence represented by tetracycline operators by analogy with the wild-type repressor; in contrast, it is regulated inversely by tetracycline.

Numerous classes of wild-type tetracycline repressors have already been described in the literature, among which classes A, B, C, D and E may be mentioned in particular. As a representative example of these repressors, the repressor termed Tn10 which belongs to class B may be mentioned more especially. According to a preferred embodiment of the invention, the repressor employed is derived from this wild-type repressor Tn10. More specifically, it is a Tn10 repressor mutated in at least one amino acid localized at position 71, 95, 101 or 102.

More preferably, it possesses wholly or partially the amino acid sequence shown as SEQ ID No. 8. It will termed TetR.

As regards the second polypeptide present in the so-called transcription activator protein, this can be any already known transcriptional activation domain. According to a preferred embodiment of the invention, it is the activation domain of herpes simplex virus protein 16, more especially the 130 amino acids of the C-terminal end of VP16, and more preferably the 11 amino acids of this C-terminal end of VP16 or alternatively peptide portions of the C-terminal portion of VP16 (Sceipel K; et al. EMBO J. 1992; 13, 4961–4968) or derivatives.

In the case of the claimed method for producing AAV, the cassette for the expression of this transcription activator is preferably integrated in the genome of a cell line 293.

According to a preferred embodiment of the invention, the expression of this transcription activator is also placed, in the cell line, under the control of a promoter which is inducible with tetracycline or one of its analogues as is defined above. More preferably, the cell line in question is a cell line 293 integrating in its genome the Op2/Tk-TetR-VP16 cassette.

The subject of the present invention is also a cell line containing in its genome a cassette for the expression of a transcription activator as defined above, comprising or otherwise an inducible promoter as defined according to the invention. More preferably, a cell line is a line integrating in its genome the Op2/Tk-TetR-VP16 cassette.

The invention also relates to the use of this type of cell line for producing adenoviruses according to the invention or AAVs.

The subject of the present invention is also a method for preparing adenoviruses containing at least one of their genes whose expression is under the control of the tetracycline-inducible promoter.

The defective recombinant adenoviruses according to the invention may be prepared in different ways.

A first method consists in transfecting the DNA of the defective recombinant virus prepared in vitro (either by ligation or in plasmid form) into a competent cell line, that is to say one carrying in trans all the functions necessary for complementation of the virus, and a transcription activator. These functions are preferably integrated in the genome of the cell, thereby enabling risks of recombination to be avoided and endowing the cell line with enhanced stability.

Thereafter, the vectors which have multiplied in the presence of a sufficient amount of tetracycline or one of its analogues are recovered, purified and amplified according to traditional techniques of molecular biology.

According to a variant of implementation, it is possible to prepare in vitro, either by ligation or in plasmid form, the DNA of the defective recombinant virus carrying the appropriate deletions, one or more viral genes under the control of a tetracycline-inducible promoter and one or more therapeutic genes. The eliminations are generally carried out on the DNA of the defective recombinant virus, by performing digestions by means of suitable restriction enzymes, followed by ligations, according to the techniques of molecular biology, as illustrated in the examples. The viral or therapeutic genes and the inducible promoter may then be inserted into this DNA by enzymatic cleavage followed by ligation, in the selected regions and in the chosen orientation. The DNA thereby obtained, which hence carries the appropriate deletions, one or more viral genes under the control of a tetracycline-inducible promoter and one or more therapeutic genes, enables the claimed recombinant adenovirus to be generated directly.

It is also possible to prepare the recombinant virus in successive steps, permitting the successive introduction of the heterologous genes and the inducible promoter. Thus, the DNA of a first recombinant virus carrying the appropriate deletions (or a part of the said deletions) and an inducible promoter such as, for example, Op2/Tk is constructed by ligation or in plasmid form. This DNA is then used to generate a first recombinant virus carrying the said deletions with an inducible promoter. The DNA of this first virus is then isolated and cotransfected with a second plasmid or the DNA of a second defective recombinant virus carrying the appropriate deletions, in particular a deletion in the E1 region, a region permitting homologous recombination and, where appropriate, a therapeutic gene. This second step thus generates the recombinant virus according to the invention.

The present invention also relates to any pharmaceutical composition comprising one or more recombinant adenoviruses as described above. The pharmaceutical compositions of the invention may be formulated with a view to topical, oral, parenteral, intranasal, intravenous, intramuscular, subcutaneous, intraocular, transdermal, and the like, administration.

Preferably, the pharmaceutical composition contains vehicles which are pharmaceutically acceptable for an injectable formulation. These can be, in particular, sterile, isotonic saline solutions (of monosodium or disodium phosphate, sodium, potassium, calcium or magnesium chloride, and the like, or mixtures of such salts), or dry, in particular lyophilized, compositions which, on adding sterilized water or physiological saline, as the case may be, enable injectable solutions to be formed.

The doses of virus used for the injection may be adapted in accordance with different parameters, and in particular in accordance with the mode of administration used, the pathology in question, the gene to be expressed or the desired period of treatment. Generally speaking, the recombinant adenoviruses according to the invention are formulated and administered in the form of doses of between $10^4$ and $10^{14}$ pfu/ml, and preferably $10^6$ to $10^{10}$ pfu/ml. The term pfu (plaque forming unit) corresponds to the infectious power of a solution of virus, and is determined by infecting a suitable cell culture and measuring, generally after 5 days, the number of plaques of infected cells. The techniques of determination of the pfu titre of a viral solution are well documented in the literature.

The adenoviruses of the invention may be used for the treatment or prevention of numerous pathologies. They are especially advantageous for the treatment of hyperproliferative pathologies (cancers, restenosis, and the like), by direct injection at the site in question. In this connection, the present invention also relates to a method for the destruction of proliferative cells, comprising the infection of the said cells or of a portion of them with an adenoviral vector as defined above. In the case where the suicide gene is a gene conferring sensitivity to a therapeutic agent, the method of destruction according to the invention thereafter comprises the treatment of the cells with the said therapeutic agent. To carry out this method, the subject of the invention is also the products comprising a recombinant adenovirus as defined above in which the suicide gene is a gene conferring sensitivity to a therapeutic agent; and the said therapeutic agent as a combination product for use simultaneously, separately or spread over time for the treatment of hyperproliferative pathologies. More especially, the suicide gene is a thymidine kinase gene and the therapeutic agent is ganciclovir or acyclovir or an analogue.

Recombinant vectors according to the invention possess especially attractive properties for use in gene therapy. These vectors combine, in effect, very superior properties of infection, safety and gene transfer capacity.

BRIEF DESCRIPTION OF THE DRAWINGS

The present invention will be described more completely by means of the examples and figures which follow, which should be considered to be illustrative and non-limiting.

Figure 1:
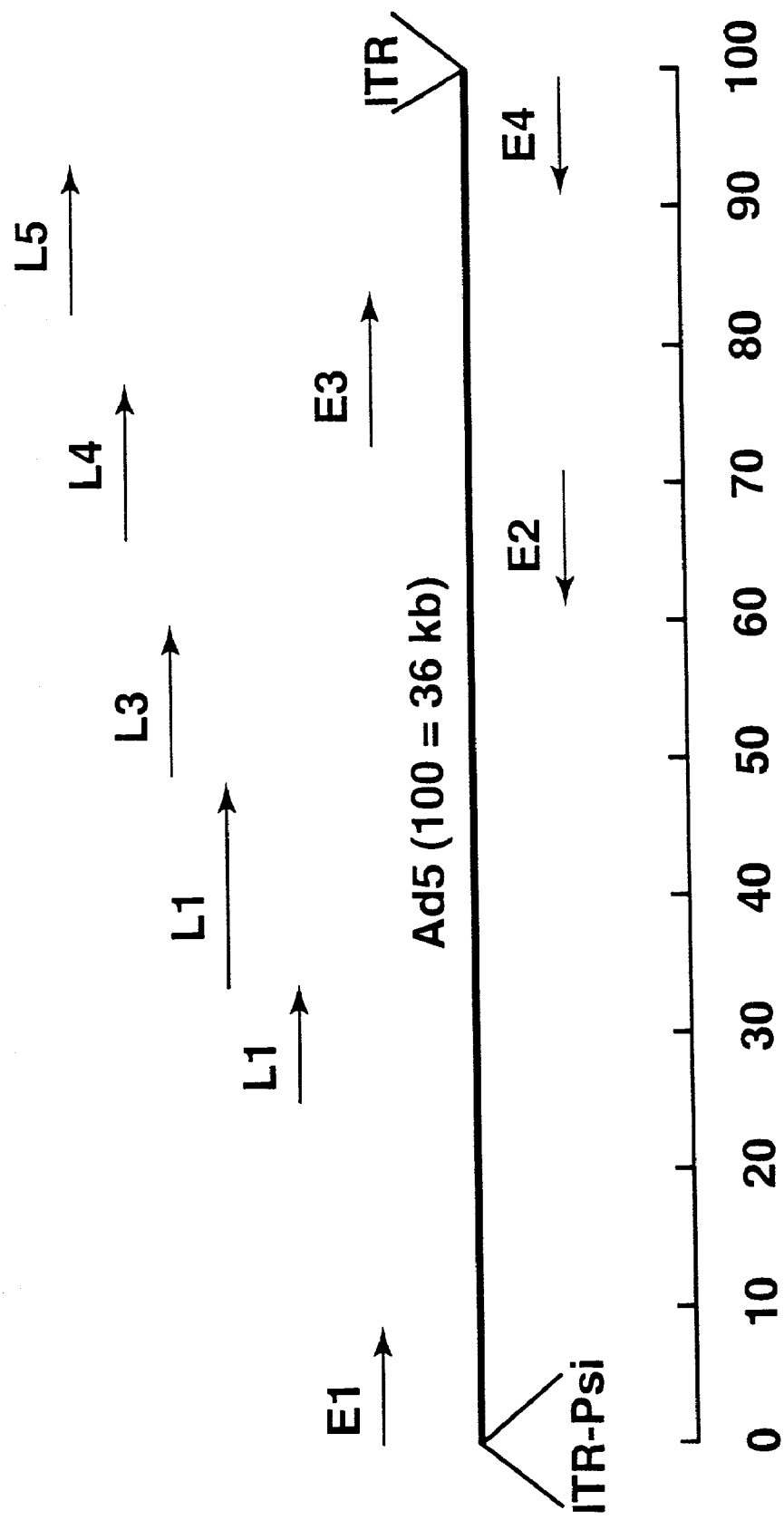
FIG. 1: Genetic organization of the Ad5 adenovirus. The complete sequence of Ad5 is available on a database, and enables a person skilled in the art to select or create any restriction site, and thus to isolate any region of the genome.
Figure 2:
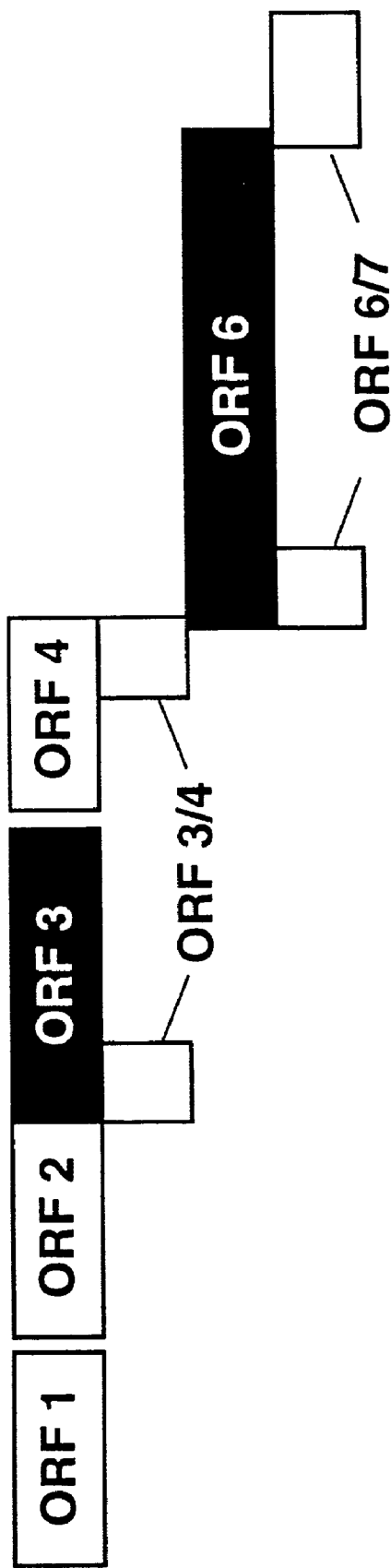
FIG. 2: Genetic organization of the E4 region.
Figure 3:
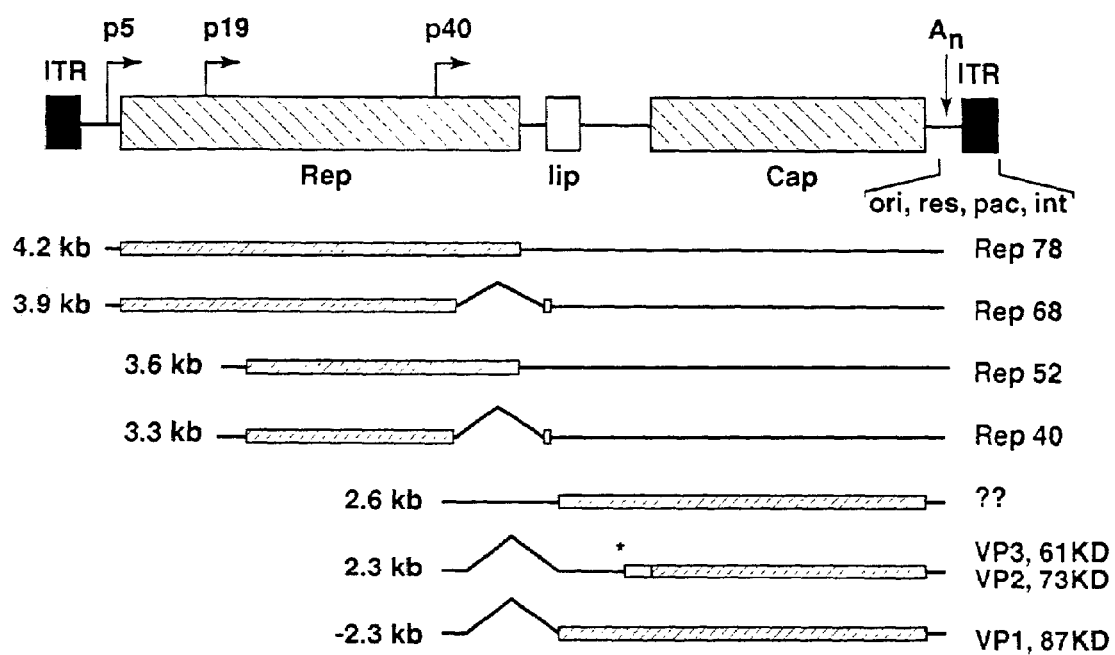
FIG. 3: Genetic organization of AAV.

DETAILED DESCRIPTION OF THE
INVENTION AND EXAMPLES

General Techniques of Molecular Biology

The methods traditionally used in molecular biology, such as preparative extractions of plasmid DNA, centrifugation of plasmid DNA in a caesium chloride gradient, agarose or acrylamide gel electrophoresis, purification of DNA fragments by electroelution, phenol or phenol-chloroform extractions of proteins, ethanol or isopropanol precipitation of DNA in a saline medium, transformation in *Escherichia coli,* and the like, are well known to a person skilled in the art and are amply described in the literature [Maniatis T. et al., "Molecular Cloning, a Laboratory Manual", Cold Spring Harbor Laboratory, Cold Spring Harbor, N.Y., 1982; Ausubel F. M. et al. (eds), "Current Protocols in Molecular Biology", John Wiley & Sons, New York, 1987].

Plasmids of the pBR322 and pUC type and phages of the M13 series are of commercial origin (Bethesda Research Laboratories).

To carry out ligation, the DNA fragments may be separated according to their size by agarose or acrylamide gel electrophoresis, extracted with phenol or with a phenol-chloroform mixture, precipitated with ethanol and then incubated in the presence of phage T4 DNA ligase (Biolabs) according to the supplier's recommendations.

The filling in of 5' protruding ends may be performed with the Klenow fragment of *E. coli* DNA polymerase I (Biolabs) according to the supplier's specifications. The destruction of 3' protruding ends is performed in the presence of phage T4 DNA polymerase (Biolabs) used according to the manufacturer's recommendations. The destruction of 5' protruding ends is performed by a controlled treatment with S1 nuclease.

In vitro site-directed mutagenesis using synthetic oligodeoxynucleotides may be performed according to the method developed by Taylor et al. [Nucleic Acids Res. 13 (1985) 8749–8764] using the kit distributed by Amersham.

The enzymatic amplification of DNA fragments by the so-called PCR [polymerase-catalysed chain reaction, Saiki R. K. et al., Science 230 (1985) 1350–1354; Mullis K. B. and Faloona F. A., Meth. Enzym. 155 (1987) 335–350] technique may be performed using a "DNA thermal cycler" (Perkin Elmer Cetus) according to the manufacturer's specifications.

Verification of the nucleotide sequences may be performed by the method developed by Sanger et al. [Proc. Natl. Acad. Sci. USA, 74 (1977) 5463–5467] using the kit distributed by Amersham.

Cell Lines Used

In the examples which follow, the following cell lines were or may be used:

Human embryonic kidney line 293 (Graham et al., J. Gen. Virol. 36 (1977) 59). This line contains, in particular, integrated in its genome, the left-hand portion of the Ad5 human adenovirus genome (12%).

KB human cell line: Originating from a human epidermal carcinoma, this line is available in the ATCC (ref. CCL17), together with the conditions enabling it to be cultured.

Hela human cell line: Originating from a human epithelial carcinoma, this line is available in the ATCC (ref. CCL2), together with the conditions enabling it to be cultured.

MDCK canine cell line: The conditions of culture of MDCK cells have been described, in particular, by Macatney et al., Science 44 (1988) 9.

gm DBP6 cell line (Brough et al., Virology 190 (1992) 624). This line consists of Hela cells carrying the adenovirus E2 gene under the control of the MMTV LTR.

EXAMPLE 1

Construction of an Adenovirus Carrying its E4 Domain Under the Control of an Op2-Tk Promoter.

1—Construction of the Plasmid pIC20H/Op2-Tk:

This plasmid carries the sequence of the Tk minimal promoter preceded by two sequences of the tetracycline operator; these sequences are recognized by the tetracycline repressor when it is bound to tetracycline.

To obtain it, the plasmid pIC20H (Marsh et al., Gene 32 (1984) 481) is digested with ClaI/BamHI, and the sequence SEQ ID No. 5, comprising two tetracycline operators upstream of a thymidine kinase minimal promoter, is introduced between these two sites.

2—Construction of the Plasmid pIC20H/ITR-Op2Tk

This plasmid is obtained by Cla1 digestion of plasmid pIC20H/Op2Tk and insertion of an Hpa2 fragment containing the Ad5 ITR (coordinates: 1/+122). This fragment comes from the commercial vector pSL1180 (Pharmacia) digested with Hind3, into which site the ITR manufactured by PCR is introduced, with Hind3 sites on each side of the amplified fragment. There is obtained in the following order: ITR-Op2-TKprom.

3—Construction of the Plasmid pIC20H/ITR-Op2Tk-E4

This plasmid corresponds to plasmid pIC20H/ITR-Op2Tk digested with Hind3, into which site the Nhe-Xba1 fragment of PY6 containing the E4 region of Ad5 is inserted. The plasmid pPY6, for its part, is obtained according to the following protocol:

A plasmid pPY2 is prepared from plasmid pIC20H. This plasmid pPY2 corresponds to the cloning of the Avr2-Sal1 fragment (approximately 1.3 kb including the MMTV promoter) of the plasmid pMSG (Pharmacia) between the Xba1 and Sal1 sites of plasmid pIC20H prepared from an *E. coli* dam+ context. The plasmid pPY4 is derived from plasmid pPY2 by deletion of a 35-bp fragment after cleavage with BamH1 and Bgl2 followed by religation. The plasmid pPY5 corresponds to plasmid pIC20H in which the Taq1-Bgl2 fragment including the E4 region of adenovirus type 5, located between positions 35576 (Taq1) and 32490 (Bgl2), has been cloned between the Cla1 and BamH1 sites. The E4 region of plasmid pPY5 is hence included in an EcoRV-Sph1 fragment which is cloned after partial digestion between the Sma1 and Sph1 sites of plasmid pPY4, thereby generating the plasmid pPY6.

4—Construction of the Plasmid pIC20H/ITR-Op2Tk-E4-L5

This is obtained by digestion of plasmid pIC20H/ITR-Op2Tk-E4 with Kpn1 and Xba1, and insertion of the 3.1-kb Kpn1-Xba1 fragment of Ad5 (coordinates: 33595–30470) containing the whole of the L5 region.

5—Construction of the Plasmid pYG4-EP

Plasmid pIC20H/ITR-Op2Tk-E4-L5 is digested with Xba1 and Nru1 to recover the corresponding fragment, which carries in order the ITR, Op2, the Tk promoter, E4 and L5. This fragment is inserted into the Xba1 and Nru1 sites of plasmid pYG4, which contains the whole of the sequence of the adenovirus from the Xba1 site to the Sph1 site. This plasmid pYG4-EP is a vector pIC20H into which the Sph1-Xba1 fragment of Ad5 (coordinates: 25095–28590) is inserted between its Sph1 and Xba1 sites.

This vector pYG4-EP, from which the E3 adenoviral region has been deleted, possesses sufficient adenoviral sequences between the Sph1 and Xba1 sites to permit complementary recombination of the adenovirus for the production of a recombinant adenovirus.

6—Construction of the Recombinant Adenovirus

This is carried out by cotransfection of 293/TetR-VP16 cells, prepared according to Example 3 below, with plasmid pYG4 linearized by Sph1 digestion and with the adenovirus RSV-βgal or an adenovirus carrying a transgene, linearized by Srf1 digestion, in the presence or absence of tetracycline. The selection and amplification of the recombinant adenovirus is then carried out according to traditional virological techniques.

EXAMPLE 2

Construction of the Recombinant Adenovirus Carrying the AAV rep-cap Genes under the Control of the Op2/Tk Promoter.

1—Construction of the Intermediate Plasmid pXL2630

This intermediate plasmid enables an EcoRI site to be introduced downstream of Op2-Tk. The presence of a restriction site at this position is of twofold interest. It serves to introduce this promoter upstream of rep-cap after the p5 promoter has been eliminated, and it also enables this hybrid promoter to be inserted upstream of TetR-VP16 for the preparation of a transformed cell line 293, as described in Example 3 below.

To this end, plasmid pIC20H/Op2-Tk, obtained according to the protocol described in Example 1, is digested with BamHI, treated with T4 DNA polymerase in order to blunt the ends and then redigested with EcoRV, and the fragment originating from this digestion and carrying the Op2-Tk promoter is introduced at the EcoRV site of the commercial plasmid pBSSK+. The orientation of the fragment is selected for the presence of an EcoRI site downstream of the promoter.

3—Introduction of an EcoRI Site at the +1 Position with Respect to Transcription of p5

To eliminate the p5 promoter, an EcoRI site is introduced at the +1 position with respect to transcription of the p5 promoter upstream of the Rep78 coding sequence by the PCR technique on the plasmid pAV2 (Laughlin C., Gene (1983), 23, 69–73). This reaction was carried out using the oligonucleotides:

SEQ ID No. 6 (seq5269): 5'GAATTCTTTTGAAGCGG-GAGGTTTGAACGCG 3' EcoRI

SEQ ID No. 7 (seq5039): 5'CTCCATGTACCTGGCTGA 3'

The fragment thus generated was introduced into pCRII (Invitrogen) to give the plasmid pMA4. The nucleotide sequence of this fragment was verified.

4—Construction of the Plasmid pMA6 Carrying the Op2-Tk-rep-cap Junction

This intermediate plasmid enables the joining of the inducible promoter with rep to be carried out. The SalI-EcoRI fragment of pXL2630 and the EcoRI-NruI fragment of pMA4 are introduced at the XhoI (compatible with SalI) and NruI sites of pIC20R (Marsh et al., Gene 32 (1984) 481) to give plasmid pMA6.

5—Construction of the Plasmid pC01 (FIG. 7 EX94008) Which Contains the Left-hand Portion of the Ad5 Adenovirus up to the HinfI Site (382), a Multiple Cloning Site and the Sau3A (3446)-NruI (6316) Fragment of the Ad5 Adenovirus 5-a/Construction of the Plasmid pCE The EcoRI-XbaI fragment corresponding to the left-hand end of the Ad5 adenovirus genome was first cloned between the EcoRI and XbaI sites of the vector pIC19H (Marsh et al., Gene 32 (1984) 481). This generates the plasmid pCA. Plasmid pCA was then cut with HinfI, its 5' protruding ends were filled in with the Klenow fragment of *E. coli* DNA polymerase I and it was then cut with EcoRI. The fragment thus generated of plasmid pCA, which contains the left-hand end of the Ad5 adenovirus genome, was then cloned between the EcoRI and SmaI sites of the vector pIC20H (Marsh et al., Gene 32 (1984) 481). This generates the plasmid pCB. Plasmid pCB was then cut with EcoRI, its 5' protruding ends were filled in with the Klenow fragment of E. coli DNA polymerase I and it was then cut with BamHI. The fragment thus generated of plasmid pCB, which contains the left-hand end of the Ad5 adenovirus genome, was then cloned between the NruI and BglII sites of the vector pIC20H. This generates the plasmid pCE, an advantageous feature of which is that it possesses the first 382 base pairs of the Ad5 adenovirus followed by a multiple cloning site.

5-b/Construction of the Plasmid pCD'

The Sau3A (3346)-SstI (3645) fragment and the SstI (3645)-NarI (5519) fragment of the Ad5 adenovirus genome were first ligated and cloned between the ClaI and BamHI sites of the vector pIC20H, thereby generating plasmid pPY53. The SalI-TaqI fragment of plasmid pPY53 prepared from a dam- context, containing the portion of the Ad5 adenovirus genome lying between the Sau3A (3346) and TaqI (5207) sites, was then cloned between the SalI and ClaI sites of the vector pIC20H, thereby generating the plasmid pCA'. The TaqI (5207)-NarI (5519) fragment of the Ad5 adenovirus genome prepared from a dam- context and the SalI-TaqI fragment of plasmid pCA' were then ligated and cloned between the SalI and NarI sites of the vector pIC20H. This generates the plasmid pCC'. The NarI (5519)-NruI (6316) fragment of the Ad5 adenovirus genome prepared from a dam- context and the SalI-NarI fragment of plasmid pCC' were then ligated and cloned between the SalI and NruI sites of the vector pIC20R. This generates the plasmid pCD'.

5-c/Construction of Plasmid pC01

A partial digestion with XhoI followed by a complete digestion with SalI of plasmid pCD' generates a restriction fragment which contains the Ad5 adenovirus sequence from the Sau3A site (3446) to the NruI site (6316). This fragment was cloned into the SalI site of plasmid pCE. This generates plasmid pC01.

6—Construction of the Plasmids pMA7 and pMA8

The EcoRV-SnaBI fragment of pMA6, carrying the AAV Op2-Tk-rep-cap-polyA+ (up to the SnaBI site, position 4495 on the AAV sequence), is introduced at the EcoRV site of pCO1 in both orientations relative to the adenovirus ITR. The plasmids thereby obtained are designated pMA7 (orientation of the cassette in the direction opposite to the adenovirus ITR) and pMA8 (same orientation).

7—Construction of the Recombinant Adenovirus Carrying Op2-Tk-rep-cap

This part describes the construction of a defective recombinant adenovirus carrying the AAV Op2-Tk-rep-cap-polyA+ cassette. This adenovirus is obtained by cotransfection of plasmid pMA7 or pMA8 with a deficient adenoviral vector, into helper cells (line 293) supplying in trans the functions encoded by the adenovirus E1 (E1A and E1B) regions.

More specifically, the adenoviruses AdMA7 and AdMA8 were prepared by homologous recombination in vivo between the adenovirus AdRSVβgal and plasmids pMA7 and pMA8 according to the following protocol: plasmid pMA7 or pMA8 linearized with NdeI and the adenovirus AdRSVBgal linearized with ClaI are cotransfected into line 293 in the presence of calcium phosphate to permit recombination. The recombinant adenoviruses thus generated are selected by plaque purification. After isolation, the recombinant adenovirus is amplified in cell line 293, leading to a culture supernatant containing the unpurified defective recombinant adenovirus having a titre of approximately 1010 pfu/ml. For the purification, the viral particles are centrifuged on a caesium chloride gradient according to known techniques (see, in particular, Graham et al., Virology 52 (1973) 456).

The adenovirus AdMA7 or AdMA8 is stored at −80° C. in 20% glycerol.

8 Construction of the Recombinant Adenovirus Carrying Op2/Tk rep-cap polyA+AAV in the E3 Region:

This part describes the construction of a recombinant adenovirus which is deleted for E1 and which carries Op2:Tk repcap polyA+AAV in the E3 region.

Plasmid pMA28 contains all of the sequence of the Ad(E1-, E3-) carrying Op2:Tk repcap polyA+AAV in the E3 region. It was constructed by means of recombination in E. Coli, by, for example, introducing the plasmid pMA24 into the strain C2110 (pXL2638) (E1-, E3-), which strain is described in application PCT/FR96/00215, which is included herein by reference.

8.1 Construction of the Intermediate Plasmid pMA22:

The Xba1—Xba1 fragment of the plasmid pMA7, carrying Op2:Tk repcap polyA+AAV, was introduced into the Xba1 site of pYG4-EP in place of the E3 region, such that Op2:Tk repcap polyA+AAV is in the inverse orientation to that of the E3 region. The plasmid which is constructed in this way is pMA22.

8.2 Construction of Plasmid pMA24, Which is Used to Perform Recombination in E. Coli:

The Nhe1-Spe1 fragment of pMA22, containing the Op2:Tk repcap polyA+AAV cassette flanked by the adenovirus 27082–28593 and 3471–31509 sequences, was introduced into the compatible site of plasmid pXL2756 in order to generate plasmid pMA24, which plasmid carries the regions required for recombination flanking the Op2:Tk repcap polyA+AAV cassette, the B. subtilis sacB gene and the gene for resistance to kanamycin.

8.3 Construction of the Recombinant Adenovirus Carrying Op2:Tk repcap polya+AAV in the E3 Region:

This construction was carried out by means of recombination in E. Coli, by electroporating plasmid pMA24 into strain C2110 (pXL2688) or C2110 (pXL2789) and selecting for a second recombination event on LB medium containing sucrose and tetracyclin. A C2110 strain harbouring plasmid pMA28 is thereby obtained.

This plasmid was then transfected, after digestion with Pac1, into 293 cells.

EXAMPLE 3

Construction of the Producing Line 293 Op2-Tk-TetR-VP16.

This part describes the construction of a 293 line carrying, integrated in its genome, the cassette of the hybrid transactivator TetR-VP16 under the control of the Op2-Tk promoter. For this purpose, the plasmid pMA2 was constructed in order to establish a line by cotransfection of this plasmid pMA2 with a plasmid pMSCV (Hawley et al. J. Exp. Med. (1993), vol. 176, 1149–1163) carrying the neomycin-resistance gene under the control of the PGK (phosphoglycerate kinase) promoter. pMA2 is constructed by inserting the SalI-EcoRI fragment of pXL2630 between the compatible XhoI-EcoRI sites of a plasmid pUHD17.1. Plasmid pUHD17.1 is a plasmid comprising the sequences coding for a mutated tetracycline repressor linked operationally to the VP16 sequence. This vector is derived from the vector pUHD15.1 (H. Bujard; P.N.A.S. U.S.A. 1992, 89, 55476–5551) which comprises the sequence of the wild-type tetracycline repressor combined with the 130 amino acids of the C-terminal end of herpes simplex virus VP16. A 399- base pair Xba1-Eco471II fragment corresponding to amino acids 3 to 135 of the mutated tetracycline repressor is exchanged for the corresponding restriction fragment of pUHD15.1 to yield pUHD17.1.

The line 293 Op2-Tk-TetR-VP16 of the invention was constructed by cotransfection of the chosen cells in the presence of calcium phosphate with plasmids pMA2 and pMSCV and a construction coding for the glucocorticoid receptor (Hollenberg et al., 1985). More specifically, line 293 cells in dishes 5 cm in diameter were transfected with 1 to 5 µg of plasmid pMA2.

Selection of Geneticin-resistant Clones

After transfection of the cells, the latter are washed, the culture medium (MEM, Sigma) supplemented with foetal calf serum (7% final) is then added and the cells are incubated for 20 hours. Next day, the cells are selected in the presence of geneticin G418 (Gibco-BRL, Life Technologies) at an effective concentration of 400 mg/l. The geneticin is changed every three days and the selectable clones appear after approximately 3 weeks. When all the untransfected cells have died, only cells which have inserted the resistance gene survive and divide to generate cell clones. When the cell clones are sufficiently large to be visible to the naked eye, they are transfer individually to the culture wells of a "24-cavity" culture plate. Each clone is then gradually amplified in the presence of geneticin, first in the wells of a "12-cavity" culture plate and then of a "6-cavity" culture plate, and thereafter amplified in cell culture dishes. Each cell clone is then stored by freezing in liquid nitrogen.

A number of clones were isolated, amplified and selected for their capacity to express a reporter gene, for example lacZ under the control of the Op2-Tk promoter after adding a suitable concentration of tetracycline. The plasmid used is pMA9, and was constructed by introducing a StuI-BamHI fragment-of pRSVgalIX carrying the sequence coding for *E. coli* β-galactosidase and a nuclear localization signal into plasmid pMA2 previously linearized with EcoRI; treated with bacteriophase T4 DNA polymerase in order to blunt its ends and then redigested with BamHI.

Among these clones, those permitting a conditional expression of rep-cap carried by the adenovirus described above and permitting AAV production at high titres were used as producing line.

The invention claimed is:

1. A recombinant adenovirus wherein a gene of viral origin is placed under the control of an inducible promoter, wherein the inducible promoter comprises a minimal promoter linked operationally to a tetracycline operator, and the tetracycline operator has the sequence as depicted in SEQ ID No: 3 or SEQ ID No: 4.

2. A recombinant adenovirus wherein a gene of viral origin is placed under the control of an inducible promoter, wherein the inducible promoter comprises a minimal promoter, wherein the minimal promoter has the sequence as depicted in SEQ ID No: 1 or SEQ ID No: 2.

3. A recombinant adenovirus wherein a gene of adenoviral origin is placed under the control of an inducible promoter, wherein the gene of adenoviral origin is from the adenovirus E2 region and is represented by a fragment chosen from the group consisting of a 72K cDNA, a 140K polymerase cDNA, and a 87K pre-terminal protein cDNA.

4. A recombinant adenovirus wherein a gene of adenoviral origin is placed under the control of an inducible promoter, wherein the gene of adenoviral origin is from the E4 region and is represented by a Taq I-BglII fragment corresponding to nucleotides 35576-32490 of adenovirus Ad5 genome.

5. The recombinant adenovirus according to claim 4, wherein the gene of adenoviral origin is from the E4 region and is represented by the BglII fragment lying-between positions 34115 and 32490 of the adenovirus Ad5 genome, containing the sequences of ORF6 and ORF7.

6. A recombinant adenovirus wherein a gene of adenoviral origin is placed under the control of an inducible promoter, wherein the adenoviral gene is from the region coding for IVa2 and is selected from the group consisting of a fragment chosen from a Bgl II-Nru I fragment corresponding to nucleotides 3328 to 6316, a Dra I-NlaI II fragment corresponding to nucleotides 4029 to 5719, and a Dra I-Xho I fragment corresponding to the fragment 4029 to 5788, on the Ad5 adenovirus sequence.

7. A recombinant adenovirus wherein a gene of adenoviral origin is placed under the control of an inducible promoter, and wherein the adenoviral gene is a gene of the E2 region, and the inducible promoter is an $Op_2$/Tk inducible promoter.

8. A recombinant adenovirus wherein a gene of viral origin is placed under the control of an Op2Tk inducible promoter, wherein the viral gene is an adeno-associated virus (AAV) gene.

9. The recombinant adenovirus according to claim 8, wherein the AAV gene encodes encapsidation functions of an adeno-associated virus (AAV).

10. The recombinant adenovirus according to claim 8, wherein the Op2/Tk inducible promoter has the sequence as depicted in SEQ ID No. 5.

\* \* \* \* \*